(12) United States Patent
Grimsby et al.

(10) Patent No.: US 8,859,215 B2
(45) Date of Patent: Oct. 14, 2014

(54) CELL BINDING ASSAY

(75) Inventors: Susanne Grimsby, Uppsala (SE); Asa Hagner-McWhirter, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 14/129,778

(22) PCT Filed: Jun. 27, 2012

(86) PCT No.: PCT/SE2012/050725
§ 371 (c)(1),
(2), (4) Date: Dec. 27, 2013

(87) PCT Pub. No.: WO2013/002721
PCT Pub. Date: Jan. 3, 2013

(65) Prior Publication Data
US 2014/0141453 A1    May 22, 2014

(30) Foreign Application Priority Data
Jun. 30, 2011 (SE) ...................................... 1150611

(51) Int. Cl.
| | | |
|---|---|---|
| *G01N 33/53* | (2006.01) | |
| *G01N 31/00* | (2006.01) | |
| *G01N 33/569* | (2006.01) | |
| *G01N 33/68* | (2006.01) | |
| *G01N 33/50* | (2006.01) | |
| *G01N 33/58* | (2006.01) | |

(52) U.S. Cl.
CPC ...... *G01N 33/56966* (2013.01); *G01N 33/6845* (2013.01); *G01N 33/5005* (2013.01); *G01N 33/582* (2013.01)
USPC .......... 435/7.21; 435/7.1; 436/501; 436/518; 424/9.1; 424/520; 422/430; 530/300; 530/350

(58) Field of Classification Search
CPC . A61K 45/06; A61K 2300/00; C12Q 1/6886; G01N 33/6893
See application file for complete search history.

(56) References Cited

FOREIGN PATENT DOCUMENTS

EP          2128266 B1     11/2012
WO   WO 2004/013632     2/2004

OTHER PUBLICATIONS

Weldon, S., et al., Analytical Biochemistry, 2008, vol. 375, pp. 156-158.
Zellner, M., et al., Electrophoresis, 2008, vol. 29, pp. 3621-3627.
Liang, X., et al., Molecular and Cellular Proteomics, 2006, vol. 5, p. S290.
Bergstrom Lind, S., et al., Biochemical and Biophysical Research Communications, 2010, vol. 401, pp. 581-585.
Patton, W. F., et al., Analytical Biochemistry, 1989, vol. 179, pp. 37-49.
Donoghue, P. M., et al., Proteomics, 2006, vol. 6, pp. 6400-6404.
Grosse, J., et al., Nuclear Medicine and Biology, 2009, vol. 36, pp. 89-98.
Colome, N., et al., Journal of Proteome Research, 2010, vol. 9, pp. 2600-2609.
Pigault, C., et al., Journal of Molecular Biology, 1994, vol. 236, pp. 199-208.
Koopman, et al., Blood, 1994, vol. 84, pp. 1415-1420.
Santini, M., et al., Critical Reviews in Oncology/Hematology, 2000, vol. 36, pp. 75-87.

*Primary Examiner* — Lisa Cook

(57) ABSTRACT

The present invention relates to a fluorescent cell binding assay combining pre-labeling and Western blotting. Intact cells are incubated with pre-labelled binders preferably followed by SDS PAGE (sodium dodecylsulphate polyacrylamide gel) separation and Western blotting. More closely, the invention relates to a cell binding assay in which the degree or amount of binding of one or more cell interacting protein or protein component to the cell surface is measured with the ability to correlate the degree of cell binding to the sample load/total number of cells.

10 Claims, 2 Drawing Sheets

CELL BINDING ASSAY

CROSS-REFERENCE TO RELATED APPLICATIONS

This application is a filing under 35 U.S.C. 371 of international application No. PCT/SE2010/050725, filed Jun. 27, 2012, published on Jan. 3, 2013 as WO 2013/002721, which claims priority to application No. 1150611-0 filed in Sweden on Jun. 30, 2011.

FIELD OF THE INVENTION

The present invention relates to a fluorescent cell binding assay combining pre-labelling and Western blotting. Intact cells are incubated with pre-labelled binders preferably followed by SDS PAGE (sodium dodecylsulphate polyacrylamide gel) separation and Western blotting. More closely, the invention relates to a cell binding assay in which the degree or amount of binding of one or more cell interacting protein or protein component to the cell surface is measured with the ability to correlate the degree of cell binding to the sample load/total number of cells.

BACKGROUND

Apoptosis is a strictly regulated process of programmed cell death in normal cells. Defects in the regulation can be related to specific disease conditions. Excessive apoptosis may be related to atrophy while insufficient apoptosis may lead to uncontrolled cell proliferation and cancer. Phospholipid phosphatidylserine (PS) is translocated from the cytoplasm to the plasma membrane upon apoptosis. Annexin V is known to bind PS and the degree of its binding to cells is therefore a good marker of apoptosis (Pigault, C., et al., J. Mol. Biol. 236, 199-208, 1994).

One common method for determination of apoptosis is to incubate cells from a subject with labelled Annexin V for measuring of PS binding on the cell surface. Flow cytometry (i.e. FASC analysis) can be used for analysing cell surface proteins including cell binding proteins (Koopman et al., Blood 84, 1415-1420, 1994). Flow cytometry is a quantitative method in which the signals are related to individual cells. There are also ELISA assays with wells coated with anti Annexin V antibodies for measuring Annexin V levels in lysed cell samples. In this case, the comparative quantitation of signal between samples relies on equal cell number without normalization. Ensuring equal sample loading is difficult. Accuracy of results relies on total protein quantification and pipetting. Another possibility for measuring protein binding to cells is to grow cells in multiwell plates, incubate cells with labelled binder, wash to remove access binder and finally measure the signals from bound protein in each well. Equal number of cells in each well is difficult to control, since cell counting and pipetting is a manual procedure involves a risk of variation number of cells seeded in each well. Moreover, the cells may grow at different rate in each well until start of incubation of binder.

SUMMARY OF THE INVENTION

The present invention provides a quantitative cell binding assay that is reliable by the possibility to normalize the signals from bound protein to a constitutively expressed endogenously protein (house-keeping protein) or total protein. The method is generally applicable to one or more cell binding proteins that interact with intact cells by binding to one or more cell surface components.

In a first aspect, the invention provides, a cell binding assay comprising a method for determining the amount of binding of a cell interacting component or components to a cell surface structure present in a cell sample, comprising
a) pre-labelling said cell interacting component with a first dye,
b) incubating said component with desired cells to allow said component to bind to cell surface structures,
c) washing away labelled cell interacting component not bound to the cells,
d) lysing the cells to form a cell lysate,
e) electrophoretic separation of proteins in said cell lysate in a gel, preferably an SDS PAGE gel,
f) transferring proteins from the gel to a Western blotting membrane,
g) Western blotting detection of housekeeping protein
h) scanning or imaging of the membrane, and
i) measuring signals from the pre-labelled cell interacting component and housekeeping protein.

Preferably the method comprises measuring the signals obtained in h) in relation to total sample load/total no of cells by probing the membrane with labelled (using a different dye than the said first dye used for the pre-labelling of the cell interacting component) binders, which could be any affinity agents such as antibodies or fragments thereof, aptamers etc., against one or more house-keeping proteins in said cell sample and by relating the signal from the cell interacting component with the signals from the house-keeping protein(s).

The method may comprise measuring the signals obtained in h) in relation to total sample load/total no of cells by pre-labelling all proteins in the cell lysate obtained in step d) with another dye than the one used for labelling of the cell interacting component, and by relating the signal from the cell interacting component with total proteins in the cell lysate.

Alternatively the method may comprise measuring the signals obtained in g) in relation to total sample load/total no of cells by post-labelling all proteins on the Western blotting membrane obtained in step f) with another dye than said first dye used for labelling of the cell interacting component.

Preferably all labelling. i.e. pre-labelling and/or post-labelling, is made with a fluorescent dye. Most preferably the dye is a cyanine dye, or any other dye enabling multiplex reactions.

In one embodiment the binder/antibody targeting housekeeping proteins is labelled/conjugated with a fluorescent dye.

The binder/antibody targeting house-keeping proteins may also be horse radish peroxidase (HRP) or alkaline phosphatase (AP) conjugated for subsequent ECL detection.

In an exemplary embodiment, the cell interacting component is Annexin V and the method is used for determination of apoptosis. However, the method is also suitable for or any other cell binding protein or protein component. The cell interacting component may bind to the cell surface of cells or fractions of cells

DETAILED DESCRIPTION OF THE INVENTION

Annexin V is a phospholipid binding protein with high affinity for PS used as a marker for apoptosis. Labelled Annexin V, such as Cy 3 conjugated Annexin V, is commonly used in ELISA and cell binding assays as well as flow cytometric apoptosis analysis.

Figure 1:
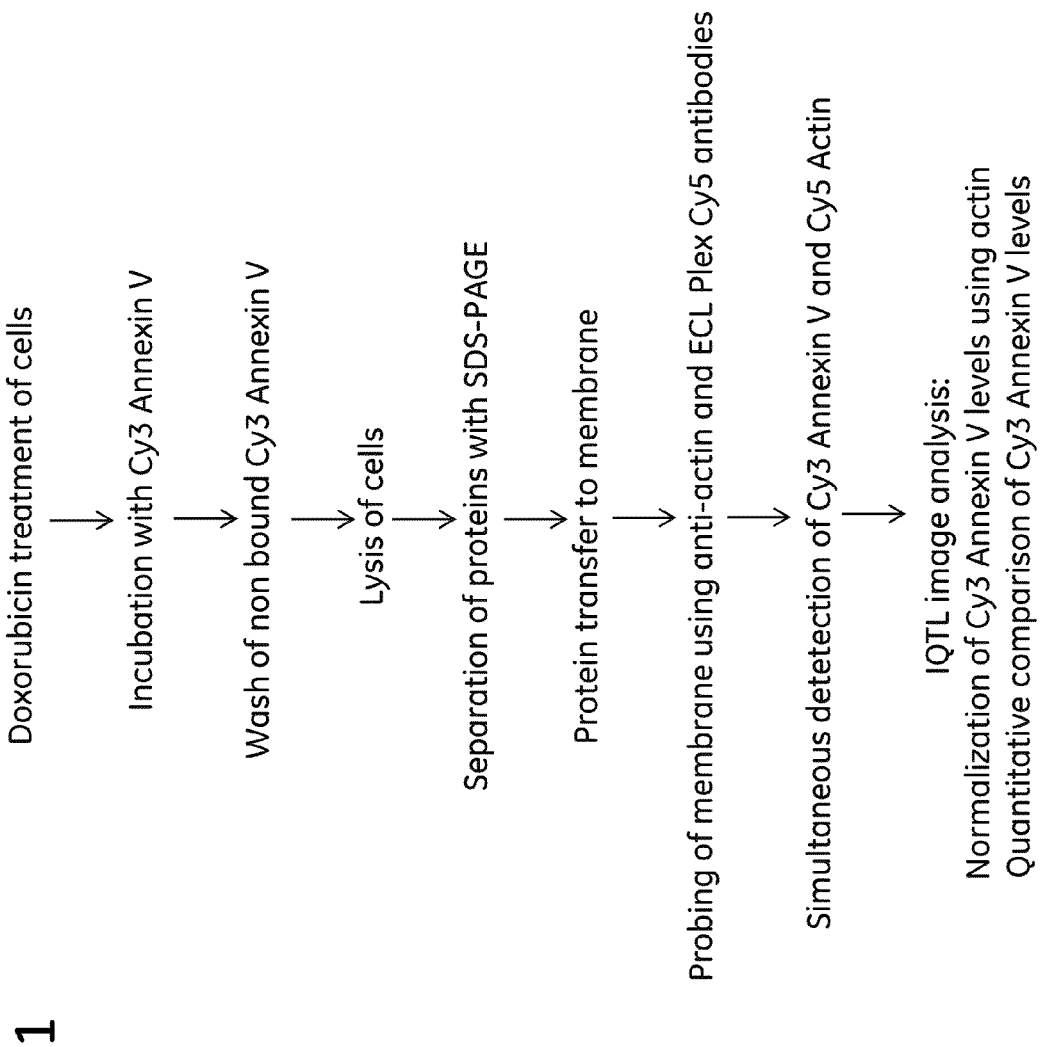
FIG. 1 shows a schematic workflow for quantitative cell binding assay using Cy3 pre-labelled Annexin V in combination with Western blotting targeting of the house-keeping protein actin with ECL Plex Cy5.

In a specific embodiment the present invention provides a fluorescent Western blotting approach for detection of labelled Annexin V binding to PS in drug treated tumor cells (FIG. 1).

The cells are incubated with Cy 3 labelled Annexin V. Instead of measuring the total signal after cell wash as in prior art, the cells are lysed after wash and subjected to SDS PAGE. Thereafter the gel is subjected to standard Western blotting procedure. The unlabelled proteins in the gel and Cy 3 labelled Annexin V (covalent bond between Cy 3 and Annexin V) is transferred onto the membrane. The membrane is then probed with primary antibody against house-keeping protein/endogenous internal standard protein reflecting sample load/number of cells and a Cy5 labelled secondary antibody for detection.

This invention offers 3 clear advantages:
1. Quantification will be very accurate, since the Annexin V signals are normalized to cell number/sample load by using endogenous standard/house-keeping (or total protein signals) signals for each sample within same lane.
2. Simultaneous multiplexed fluorescence detection of up to 3 binding targets, and in addition endogenous standard or house-keeping target (using Cy 2, Cy 3, Cy 5 and Cy7) with broad dynamic range and sensitivity.
3. Possibility to confirm the Mw size and the quality of Annexin V.

The procedure/method of the invention can be applied to any type of cell binding assay that measure the binding of a labeled molecule to cells. Furthermore, the method is of great advantage for multiplex application with use of fluorescent pre-labelling of cell interacting proteins in combination with Western blotting in an area of large general interest.

This method according to the invention will improve the accuracy for quantification of the Annexin V signals by the possibility to normalize signals. Analysis of multiple binders simultaneously by multiplexing is also great advantage. Compared to current methods, this new alternative approach will also give information on Mw which makes it possible to specifically quantify the signals of the labelled protein.

Experimental Part

The method in according to the invention can be widely applied in applications were protein binding to cells is being analysed. The method is exemplified below in a method for an apoptosis assay.

Doxorubicin is an anti-cancer drugs aimed to inhibit uncontrolled cell proliferation by inducing apoptosis in cells. Multicellular Tumor Spheroids were treated with Doxorubicin and incubated with Cy 3 Annexin V. The cells are lysed and the proteins are separated and transferred to a membrane. Cy 3 Annexin V can be detected simultaneously with actin targeted by ECL Plex Cy5 Western Blotting. The amount of Annexin V binding to the cells upon treatment can easily be quantified after normalization to the house-keeping protein actin.

Cancer cells, Multicellular Tumor Spheroids (MTS) (Sanitini et al. *Critical Rev Oncol Hematol* 2001, 36:75-87) were treated for 3 days with four different concentrations (1 µM, 5 µM and 10 µM) of the cancer drug Doxorubicin. To determine the level of drug induced apoptosis the cells were incubated with Cy3 conjugated Annexin V. Non-bound Cy 3 Annexin V was washed away with PBS followed by cell lysis using mammalian cell protein extraction buffer (GE Healthcare). The total cell lysate was subjected to SDS-PAGE using precast 12% Novex Tris Glycine gels (Invitrogen) followed by protein transfer to Hybond LFP membrane (GE Healthcare). The membrane was blocked using 2% ECL Advance blocking agent (GE Healthcare) in PBST, washed in PBST, incubated with mouse anti-actin primary antibody (Sigma, diluted 1:750) and ECL Plex Cy5 anti-mouse IgG antibody (GE Healthcare, diluted 1:2500) for detection of actin known as a housekeeping protein.

Figure 2:
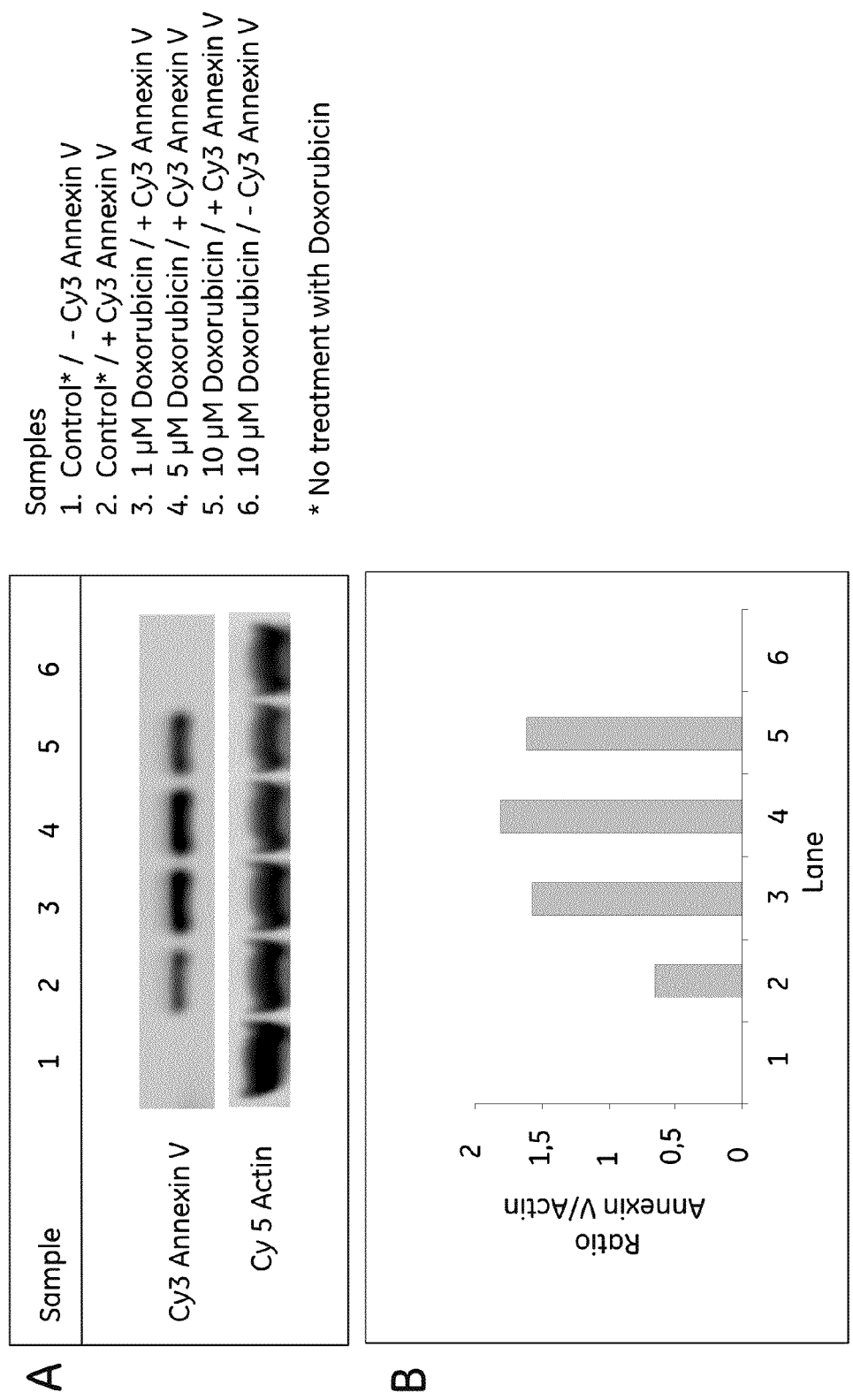
FIG. 2 shows cells incubated with different concentrations of doxorubicin and Cy3 Annexin V (lane 1-5), washed and subjected to Western blotting. Cy3 pre-labelled Annexin V (upper panel) and the house-keeping protein actin targeted with ECL Plex Cy5 (lower panel) were detected simultaneously on the Western membrane by scanning using a fluorescence imager (A). Annexin V signals are normalized (corrected) against the signals of the house-keeping protein actin. The Cy3:Cy5 ratio is plotted for each sample for quantitative comparison of Annexin V binding to cells (B).

The signals from bound Cy 3 Annexin V and Cy 5 actin are detected simultaneously by scanning the membrane in Cy3 and Cy5 channels using a Typhoon Imager (GE Healthcare, FIG. 2a). The image was analysed with Image Quant TL software (GE Healthcare). The Cy 3 Annexin V signals are normalized to actin (house-keeping protein). The ratio between Cy3 Annexin V and Cy 5 actin was plotted in a bar diagram (FIG. 2b). In this way any uneven sample loading is corrected for and very accurate quantification of the cells capacity to bind Annexin V is determined. See workflow FIG. 1.

Results

Apoptosis is induced as a response to Doxorubicin treatment and Annexin V binds to PS at the cell surface of apopotic cells. In this assay we show a dose dependent binding of Annexin V to treated cells indicating an increased apoptosis of the drug treated cells. Cy 3 labeled Annexin V (covalent bond between dye and protein) is transferred onto the membrane and detected directly on the membrane without any antibody probing. Actin is detected using ECL Plex Cy 5 Western Blotting. To quantify the Annexin V binding, the signal ratio between Annexin V and actin is plotted (FIG. 2b). The Annexin V binding at different doses can be quantitatively compared against the control (no treatment).

The results show a Doxorubicin dose dependent Annexin V binding to cells up to 5 µM, indicating increased apoptosis. Higher dose of Doxorubicin seems to be toxic for the cells causing necrosis rather than apoptosis. This explains the decrease of the Annexin V binding at treatment with 10 µM Doxorubicin.

The invention claimed is:

1. A method for determining the amount of binding of a cell interacting component to a cell surface structure present in a cell sample, comprising:
   a) pre-labelling said cell interacting component with a first dye;
   b) incubating said component with desired cells to allow said component to bind to cell surface structures;
   c) washing away labelled cell interacting component not bound to the cells;
   d) lysing the cells to form a cell lysate;
   e) electrophoretic separation of proteins in said cell lysate in a gel, preferably a SDS PAGE gel;
   f) transferring proteins from the gel to a Western blotting membrane;

g) Western blotting detection of housekeeping protein;
h) scanning or imaging of the membrane; and
i) measuring signals from the pre-labelled cell interacting component and housekeeping protein.

2. The method of claim 1, comprising measuring the signals obtained in step h) in relation to total sample load/total no of cells by probing the membrane with labelled (using a different dye than the said first dye used for the pre-labelling of the cell interacting component) binders/antibodies against one or more house-keeping proteins in said cell sample and by relating the signal from the cell interacting component with the signals from the house-keeping protein(s).

3. The method of claim 1, comprising measuring the signals obtained in h) in relation to total sample load/total no of cells by pre-labelling all proteins in the cell lysate obtained in step d) with another dye than the one used for labelling of the cell interacting component, and by relating the signal from the cell interacting component with total proteins in the cell lysate.

4. The method of claim 1, comprising measuring the signals obtained in g) in relation to total sample load/total no of cells by post-labeling all proteins on the Western blotting membrane obtained in step f) with another dye than said first dye used for labelling of the cell interacting component.

5. The method of claim 1, wherein all labelling is made with a fluorescent dye.

6. The method of claim 5, wherein the dye is a cyanine dye, or any other dye enabling multiplex detection.

7. The method of claim 1, wherein the binder/antibody targeting house-keeping proteins is labelled/conjugated with a fluorescent dye.

8. The method of claim 1, wherein the binder/antibody targeting house-keeping proteins is conjugated with horse radish peroxidase (HRP) or alkaline phosphatase (AP) or similar enzyme for subsequent ECL detection.

9. The method of claim 1, wherein the cell interacting component is Annexin V or any other protein or protein component.

10. The method of claim 1, wherein the cell interacting component is binding to cell surface of cells or fractions of cells.

* * * * *